US00PP31610P2

(12) United States Plant Patent
Shipley

(10) Patent No.: US PP31,610 P2
(45) Date of Patent: Mar. 31, 2020

(54) ***TECOMA* HYBRID PLANT NAMED 'RED HOT'**

(50) Latin Name: ***Tecoma* hybrid**
Varietal Denomination: Red Hot

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 0 days.

(21) Appl. No.: 16/350,157

(22) Filed: Oct. 9, 2018

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
CPC ..... A01H 5/02; A01H 6/00
See application file for complete search history.

*Primary Examiner* — Keith O. Robinson

(57) ABSTRACT

Compact, upright, bush form, red flower clusters, and lack of seed production characterize a new and distinct *Tecoma* hybrid named 'Red Hot'. *Tecoma* hybrid 'Red Hot' blooms throughout the warm season (average daytime highs exceeding 70° F.).

4 Drawing Sheets

Latin name: *Tecoma* hybrid 'Red Hot'.
Varietal denomination: 'Red Hot'.

BACKGROUND OF THE INVENTION

Plants of the genus *Tecoma* have been grown as landscape plants for many decades. These plants typically have bright green leaves and large trumpet shaped flowers that attract hummingbirds and bees. The most common species grown has been *Tecoma stans*, the most widely distributed of the genus, growing from the tropics and subtropics of South America to the warmer parts of the American Southwest. There are reportedly 14 species of *Tecoma*, mostly native to the Andean region. This number has come into question in recent research, as the actual number may only be half that estimate since many of the species are highly variable and interspecies hybrids appear to be fairly common in nature. Several of the South American species with red or orange flowers have been hybridized with *Tecoma stans*. Many of these hybrids have been patented beginning in 2007. Many of the hybrids have reduced fertility, with the culturally desirable result of less fruit production and trash in the landscape. Many of the hybrids incorporate the orange or orange-red characteristics typical of some of the Andean species. The present invention relates to a new and distinct cultivar of *Tecoma* hybrid. The cultivar originated as a chance seedling of unknown hybrid origin, with both male and female parents unknown, which germinated at a nursery near Sahuarita, Ariz. and is the object of this application.

SUMMARY OF THE INVENTION

Among the features that distinguish the new *Tecoma* cultivar from all other available and commercial varieties of *Tecoma* known to the inventor are the following combination of characteristics: compact bush form, red flower clusters, leaves with mostly 5-9 leaflets and lack of seed production. *Tecoma* hybrid 'Red Hot' blooms throughout the warm season (average daytime highs exceeding 70° F., specifically from roughly April-early November).

The propagation procedure is as follows: Four-inch long cuttings are taken from semihardwood branches and placed into DIP'N GRO™ (1:10 water mixture) for 15 seconds. The plants are then placed into growing medium and moved to a fog house with humidity controlled between 85-93% relative humidity at a temperature between 65-85° F. First roots appear in about a month with rooting essentially complete within 8 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Tecoma* hybrid 'RRRRR' growing near Sahuarita, Ariz., depicted in color as nearly correct as it is possible to make in a color illustration of the character.

DETAILED PLANT DESRIPTION

Figure 1:
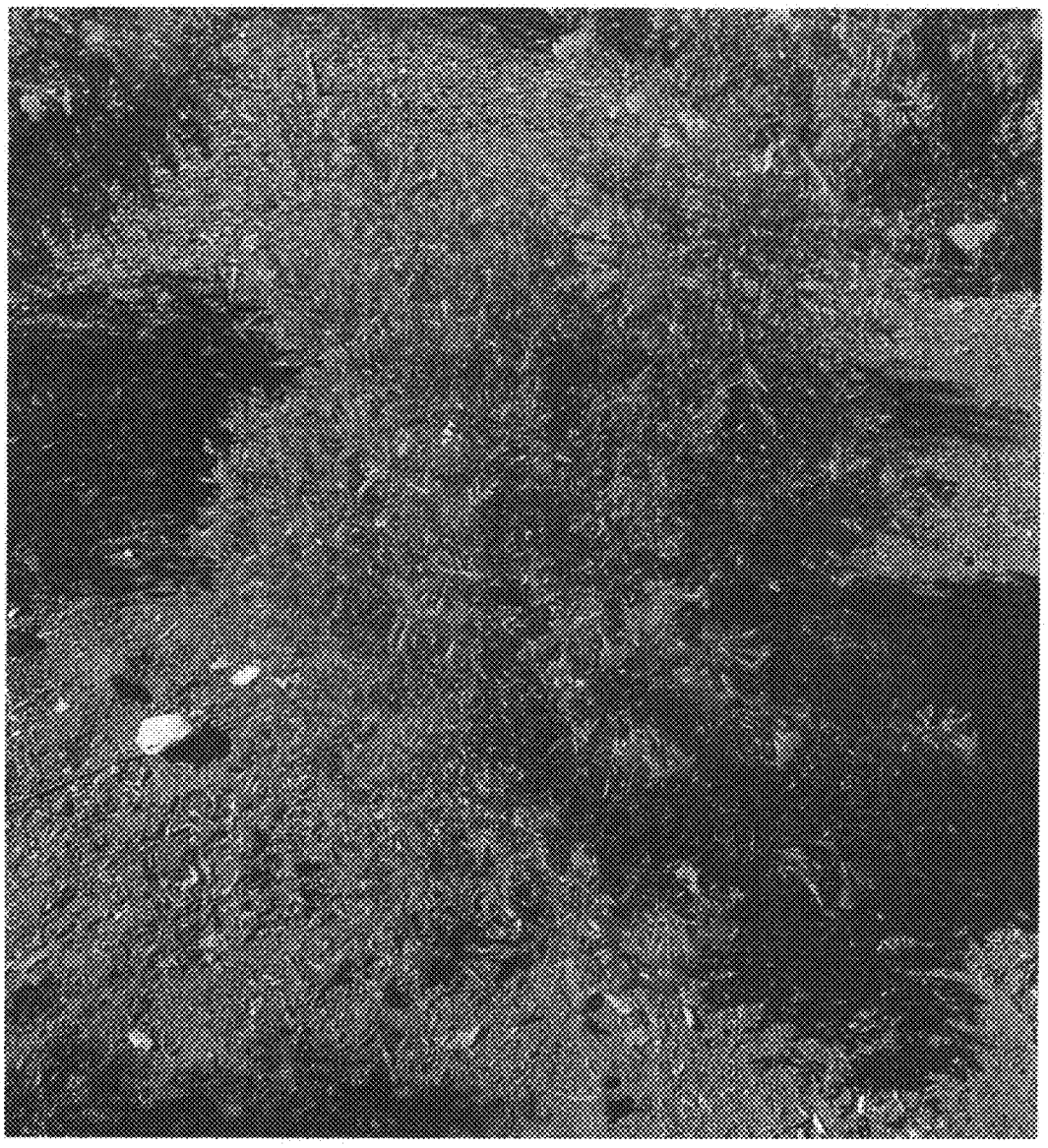
FIG. 1 shows a *Tecoma* hybrid 'Red Hot' plant aged 3 years from rooted cutting growing near Sahuarita, Ariz.
Figure 2:
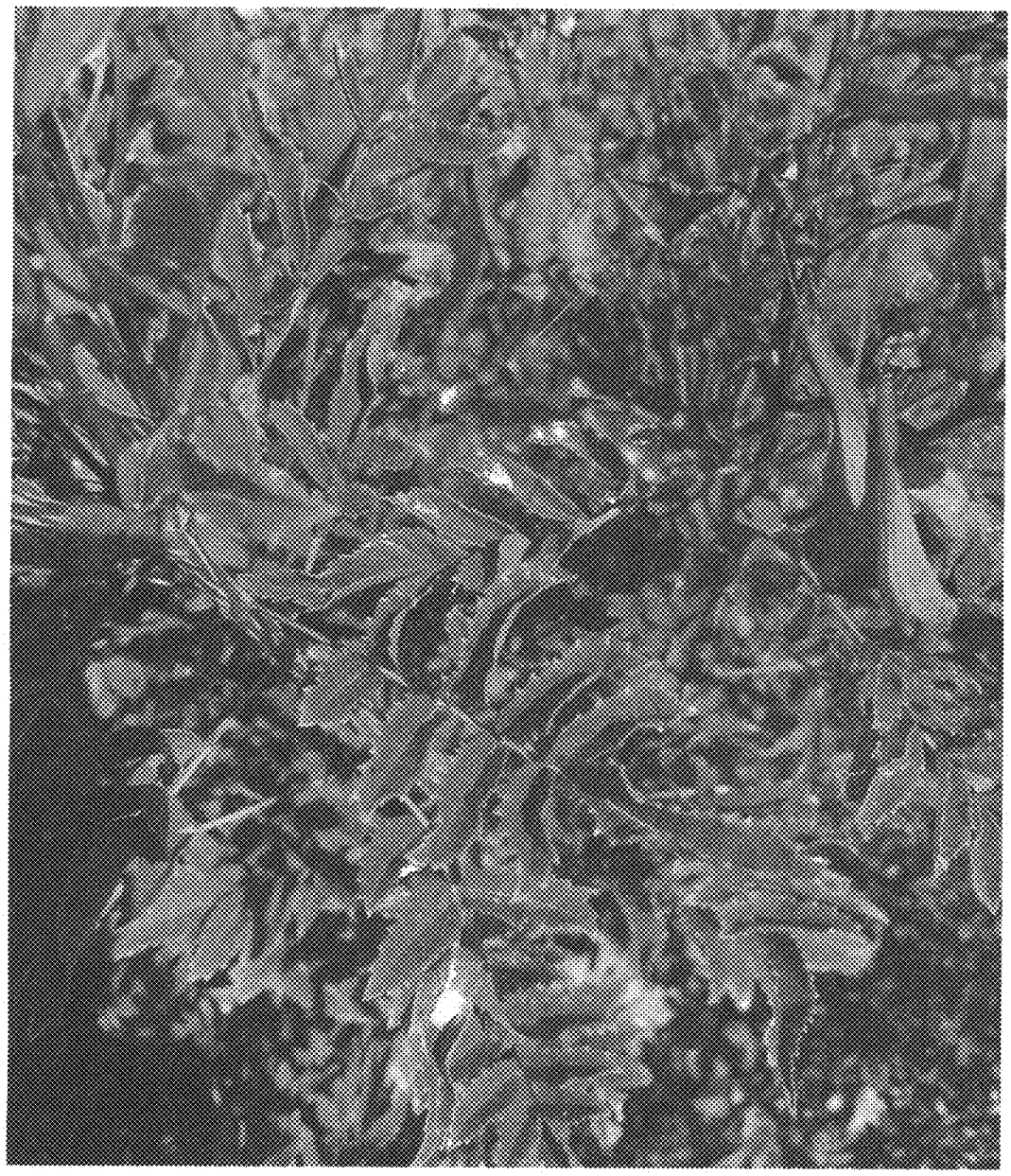
FIG. 2 shows the leaves of *Tecoma* hybrid 'Red Hot'.
Figure 3:
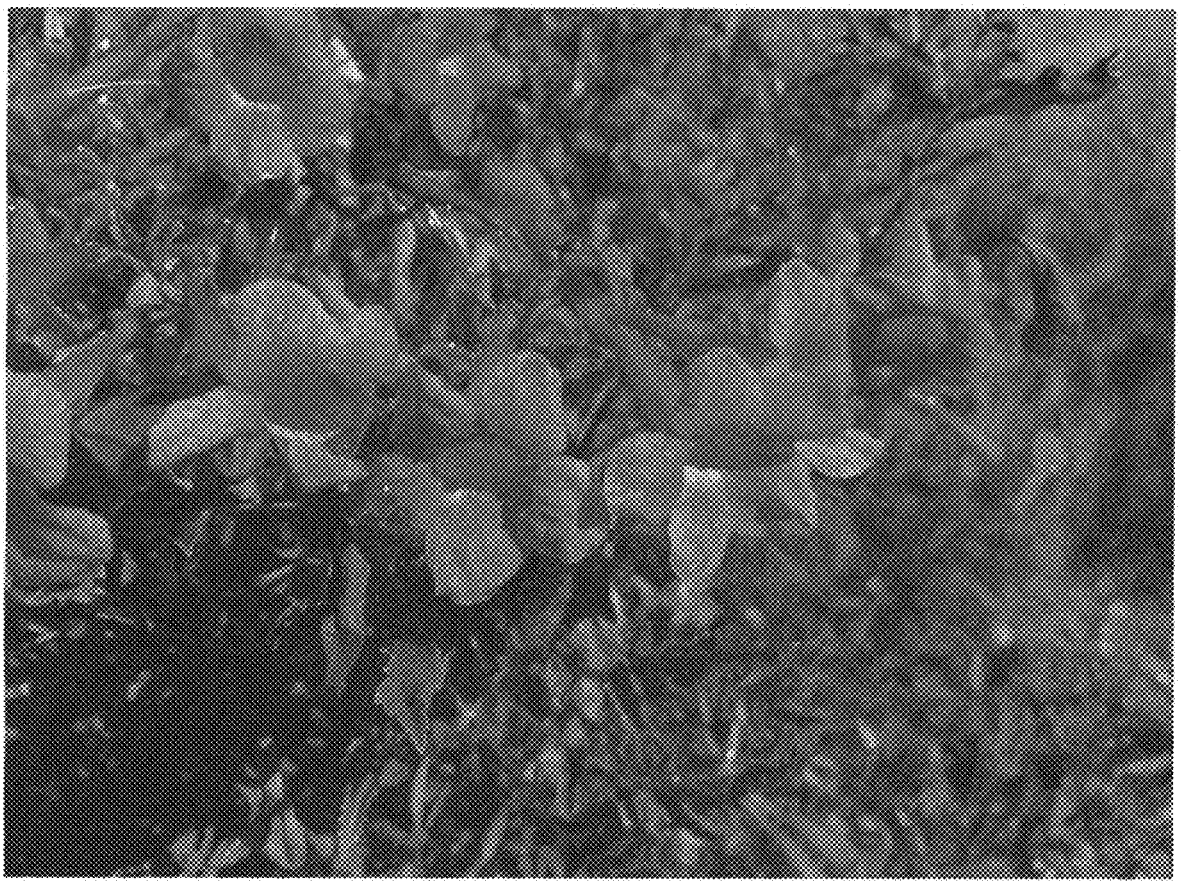
FIG. 3 shows flowers and inflorescences of *Tecoma* hybrid 'Red Hot'.
Figure 4:
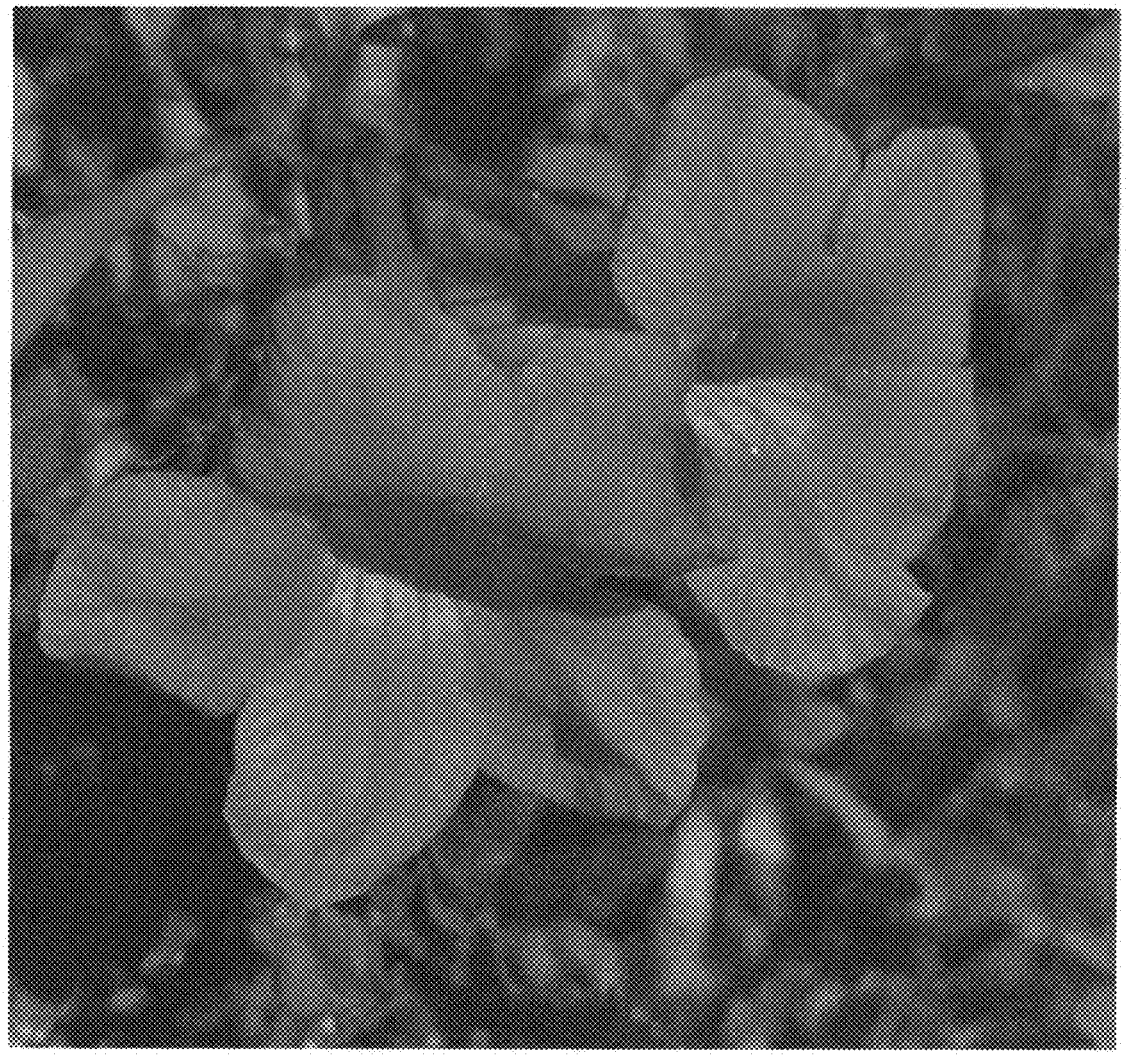
FIG. 4 is a closeup of the flowers of *Tecoma* hybrid 'Red Hot'.

The following is a detailed description of the new *Tecoma* plant based upon a plant at age 3 from a cutting growing near Sahuarita, Ariz. The color descriptions are based upon the 5$^{th}$ edition R.H.S. Colour Chart, 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

*Tecoma* hybrid 'Red Hot' is a highly branched, upright, compact, leafy shrub about 3 feet tall×2.5 feet wide at age 3. The plants are dense in appearance. Branch angle ranges from 25-45°. Young stems are obscurely and sparsely puberulent, mostly near the nodes. Frequently two branches are produced at each node. Branches are very strong. The plant examined had about 300 branches. Branch color varies from 144A on the shaded to N77A on the sunward side. Lenticels are absent. Young stems measure 2-3mm in diameter. Internode length ranges from 15-45 mm. The largest older stems are up to 16 mm in diameter, color 164D.

Roots were observed on rooted cuttings. Young roots are fine, 1 mm or less in diameter, and moderately strongly branching. Root growth is relatively erratic, tending downward. Young roots are colored 159C.

Leaf arrangement is opposite, the leaves odd pinnately compound, with (3) 5-9 leaflets, mostly with 7 leaflets. Leaves are ascending and diverge from the stem axis at an angle of about 45° Leaf adaxial surface is glabrous, glossy, bordering on resinous, color 147A. Leaf abaxial surface glabrous, glossy, but less so than adaxial surface, color 147B. Leaves measure 5.5-11 cm long, 2.5-4cm wide. Leaflets measure 6-12 mm wide×16-32 mm long. The apical leaflet is always the largest and usually has a slight twist. Leaflet margins are serrate, leaflets variously upwardly folded or cupped along the leaflet midrib. Leaflet shape is more or less elliptical, base and tip both acute. Leaflet tips mostly slightly apiculate. Leaflet bases vary from equally to obliquely acute. Leaflets have net venation with main veins arranged pinnately. Veins are slightly depressed adaxially and raised abaxially. Leaflets are colored 147A adaxially and 147B abaxially. Leaves are without a discernable fragrance. The plant examined had about 2500 leaves.

Stipules none. Active axillary buds glabrous, dorsally compressed, 2 mm long×1.5 mm wide×1 mm thick. Dormant/undeveloped axillary buds obscure, less than 1 mm.

Petiole is semicircular in cross section, with a raised nerve on either edge of the flat (adaxial) side, petiole surface glabrous, slightly resinous. The petiole diverges from the stem axis at an angle of about 45°. Petiole color ranges from 144A to 146C, sometimes tinged with 61A along the petiole margins and bases on sunward leaves. Petiole measures 16-30 mm long, 0.75-1.6 mm wide. Leaf rachis similar to petiole in color and shape.

Inflorescence is terminal not deviating from the stem axis. On first examination the inflorescence appears racemose, but is actually a reduced panicle. Peduncle 2 mm in diameter× 6-13 mm in length, slightly tapering, color grading from N77A on the sunward side to 144A on the shaded side. The peduncle surface is glabrous and slightly resinous. The peduncle is moderately strong at the time of anthesis. Peduncle bracts 2, these stipule-like, located below the pair of leaves at the inflorescence base, these bracts 4 mm long×0.75 mm wide, color 144B. Pedicellar bracts 2, 1 mm long×0.25 mm wide, color 144B. Floral branch bract 1, 2 mm long×0.75 mm, color 144B. Inflorescence is subsecund, typically 6-13 cm long×10 cm in diameter, each inflorescence producing from 7-25 flowers. Sub pedicellar inflorescence branches measure 6-9 mm long, 1-1.5 mm in diameter, terete, glabrous, color 144B. Pedicels measure 4-7 mm long, 1 mm in diameter, terete, glabrous, color 144B. Pedicels diverge from the inflorescence axes at 45-60°. Mature buds are 38-43 mm long, 7-9 mm at the widest point. Bud with an angular pentagonal bulge at the tip, color 46A, grading to 34A along the tube. The bud is somewhat upcurved. Flowers are 40-50 mm long×28-30 mm wide. Flowers last 2-3 days and then fall away within a week. Flowers are slightly fragrant. Flowers are bilabiate, upcurved, trumpet shaped with 5 more or less dentate petal lobes, color 46A (both surfaces), the 2 upper lobes reflexed, 3 lower petals extended, then curving somewhat backward at the apex. Corolla tube lineoid from base for 11 mm, 2 mm diameter, then flaring to 10-11 mm at the limb, tube color 46C. Interior of corolla with numerous (17-21) guidelines colored as the corolla lobes (46A) on an orange background (23B). Corolla lobes measure 8-10 mm long×9-11 mm wide. The lobes are rounded in shape and slightly constricted at the fused portion of the corolla. The petal lobe margin is entire. The lobes are slightly crisped and are glabrous. Calyx regular, 5-6 mm long×3mm wide at the widest point, more or less campanulate, the tube slightly angled, glabrous, color varying from N77A on the sunward side to 144B on the shaded side. Calyx is lobed, the lobes carinate, apiculate, glabrous, about 3 mm long×2 mm wide, color 144B.

Stamens: 4 normal and 1 vestigial. Normal stamens are attached to the corolla for about 15 mm, then free for an additional 10-14 mm, filament diameter 0.75 mm at the attachment point, then tapering toward the anther, filament color 13C. Anthers basifixed, dehiscing longitudinally from the base, the thecae spreading before anthesis, apparently with little or no pollen, the pollen colored 11B. Open anthers about 5 mm long, 1 mm wide, color 11B. Pistil is superior, single, measuring from 27-30 mm in length, with 2 carpels. Ovary lance/lineoid, measuring 4.5 mm long×1 mm in diameter, color 144C, abruptly tapering to the style. Style is 22-25 mm long, color 154C. Stigma strongly laterally compressed, diamond shaped, about 1 mm, color 154B.

Fruits were not seen; the plant is apparently at least mostly sterile.

*Tecoma* hybrid 'Red Hot' is not cold hardy and is damaged by frost. The plants are root hardy to about 20°. Bloom season runs from about April to mid November in the area of the evaluated specimen. Pest and pathogens: none noted.

COMPARISONS TO RELATED *TECOMAS*

The number of *Tecoma* cultivars has increased substantially in the last 20 years. Below *Tecoma* hybrid 'Red Hot' is compared to other patented cultivars.

Compared to *Tecoma* 'Sunhorteaka' (U.S. Plant Pat. No. 27,372), *Tecoma* hybrid 'Red Hot' differs most notably having larger, redder buds and flowers. The flowers of *Tecoma* 'Sunhorteaka' are, however, slightly larger in diameter at the apex of the flower. Leaves of *Tecoma* hybrid 'Red Hot' are considerably smaller than those of 'Sunhorteaka' with mostly 5-9 leaflets compared to 3-5 with 'Sunhorteaka'.

Compared to *Tecoma* 'Sunhorteki' (U.S. Plant Pat. No. 27,373), *Tecoma* hybrid 'Red Hot' differs most notably having red flowers as opposed to predominantly yellow flowers with 'Sunhorteki' as well as having mostly 5-9 leaflets compared to 3-5 on 'Sunhorteki'.

Compared to *Tecoma* 'Mnstapbe' (U.S. Plant Pat. No. 20,246), *Tecoma* hybrid 'Red Hot' differs most notably having red flowers as opposed to yellow-orange with 'Mnstapbe' as well as having mostly 5-9 leaflets compared to 3-5 with 'Mnstapbe'.

Compared to *Tecoma* 'TEC60109105' (U.S. Plant Pat. No. 24,169), *Tecoma* hybrid differs most notably having red flowers as opposed to yellow flowers with 'TEC60109105' as well as having mostly 5-9 leaflets compared to 7-11 with 'TEC60109105'.

Compared to *Tecoma* 'TEC6010916' (U.S. Plant Pat. No. 24,170), *Tecoma* hybrid 'Red Hot' differs most notably in having red flowers compared to orange-red with 'TEC6010916' as well as having mostly 5-9 leaflets compared to 9-11 with 'TEC6010916'.

Compared to *Tecoma* 'Sunhortedai' (U.S. Plant Pat. No. 29,169), *Tecoma* hybrid 'Red Hot' has redder flowers, leaves with typically 7 leaflets compared to 5 or 7 for 'Sunhortedai'. Also, the leaves of 'Red Hot' are only about a third as wide and smaller overall compared to 'Sunhortedai'.

Compared to *Tecoma* 'Balbahelor' (U.S. Plant Pat. No. 30,633) and 'Balbahel' (U.S. Plant Pat. No. 30,667), 'Red Hot' may be easily separated as the flower colors of both 'Balbahelor' and 'Balbahel' fall within the yellow flower group and the flowers of 'Red Hot' fall within the red color group.

I claim:

1. A new and distinct *Tecoma* plant substantially as described and illustrated herein.

* * * * *